United States Patent [19]
Phelps

[11] Patent Number: 5,827,221
[45] Date of Patent: *Oct. 27, 1998

[54] NEEDLE DEVICE

[76] Inventor: David Y. Phelps, 2815 Stratford Ave., Louisville, Ky. 40207

[ * ] Notice: The term of this patent shall not extend beyond the expiration date of Pat. No. 5,207,647.

[21] Appl. No.: 643,470

[22] Filed: May 6, 1996

Related U.S. Application Data

[60] Continuation of Ser. No. 361,982, Dec. 22, 1994, Pat. No. 5,514,111, which is a division of Ser. No. 57,354, May 3, 1993, Pat. No. 5,376,082, which is a continuation-in-part of Ser. No. 788,253, Nov. 5, 1991, Pat. No. 5,207,647.

[51] Int. Cl.[6] .................................................. A61M 31/00
[52] U.S. Cl. .............................. 604/51; 604/49; 604/164
[58] Field of Search .................................... 604/169, 167, 604/158, 274, 256, 248, 246, 28, 49, 51

[56] References Cited

U.S. PATENT DOCUMENTS

| 4,601,710 | 7/1986 | Moll | 604/274 |
|---|---|---|---|
| 4,654,030 | 3/1987 | Moll et al. | 604/165 |
| 4,869,717 | 9/1989 | Adair | 604/274 |
| 4,931,042 | 6/1990 | Holmes et al. | 604/164 |
| 5,104,382 | 4/1992 | Brinkerhoff et al. | 604/165 |
| 5,116,353 | 5/1992 | Green | 604/164 |
| 5,158,552 | 10/1992 | Borgia et al. | 604/274 |
| 5,207,647 | 5/1993 | Phelps | 604/158 |
| 5,376,082 | 12/1994 | Phelps | 604/158 |

Primary Examiner—Wynn Wood Coggins
Assistant Examiner—N. Kent Gring
Attorney, Agent, or Firm—Don Halgren

[57] ABSTRACT

A needle device for the delivery of medicaments, insuflation or other medical devices, having a reciprocable needle sensitive to lack of resistance, whereupon such needle retracts, permitting a cannula therewith to provide access to the penetrated body.

2 Claims, 6 Drawing Sheets

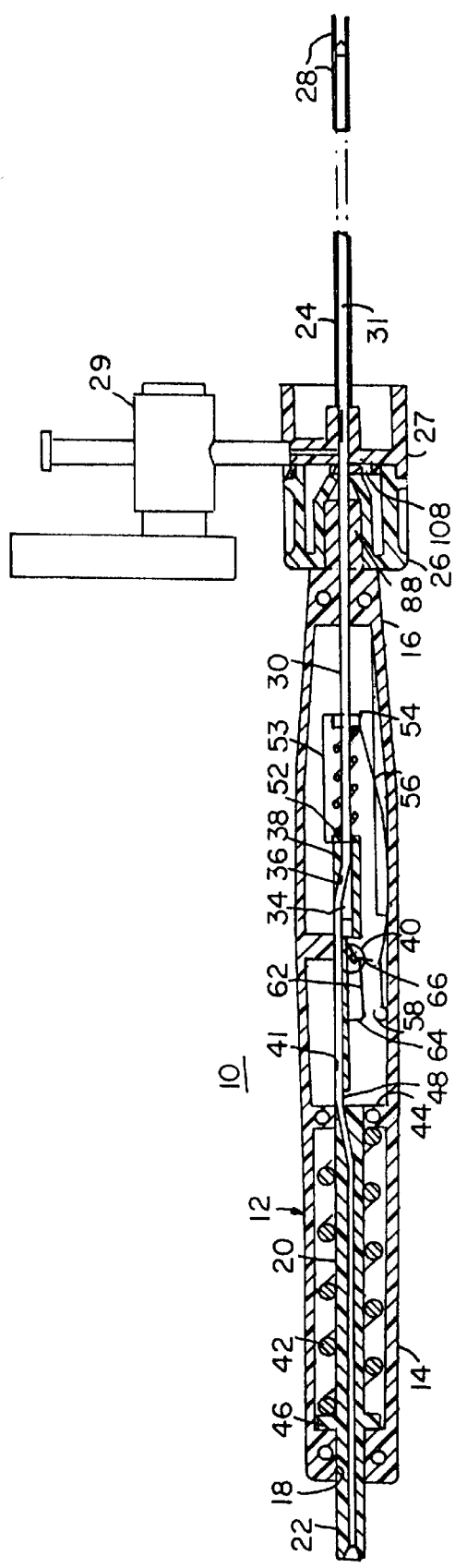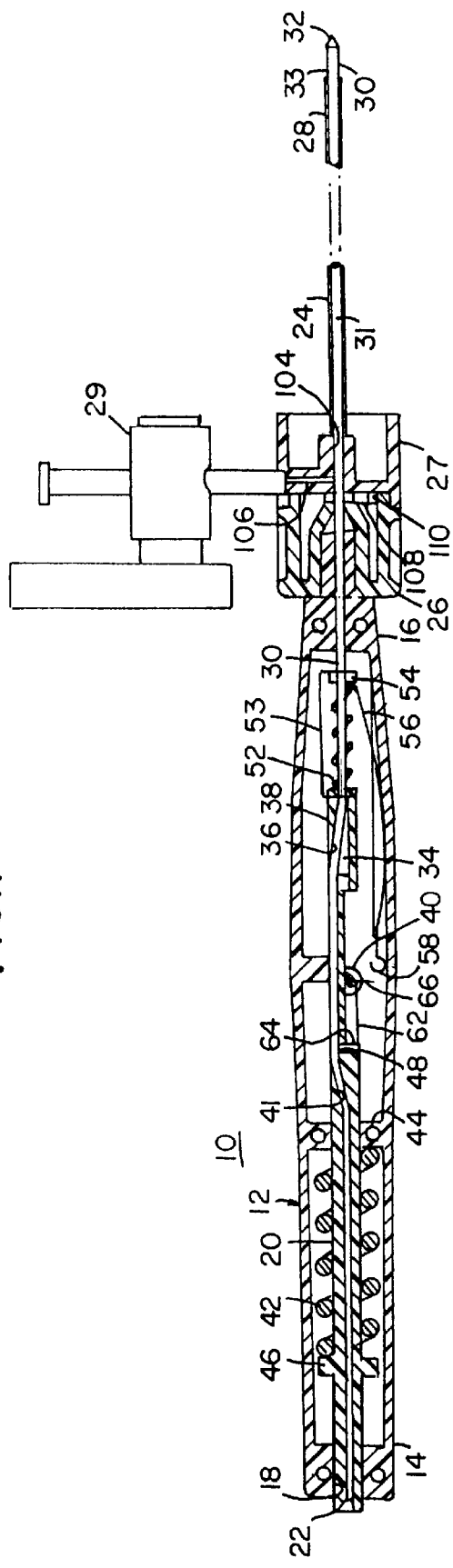

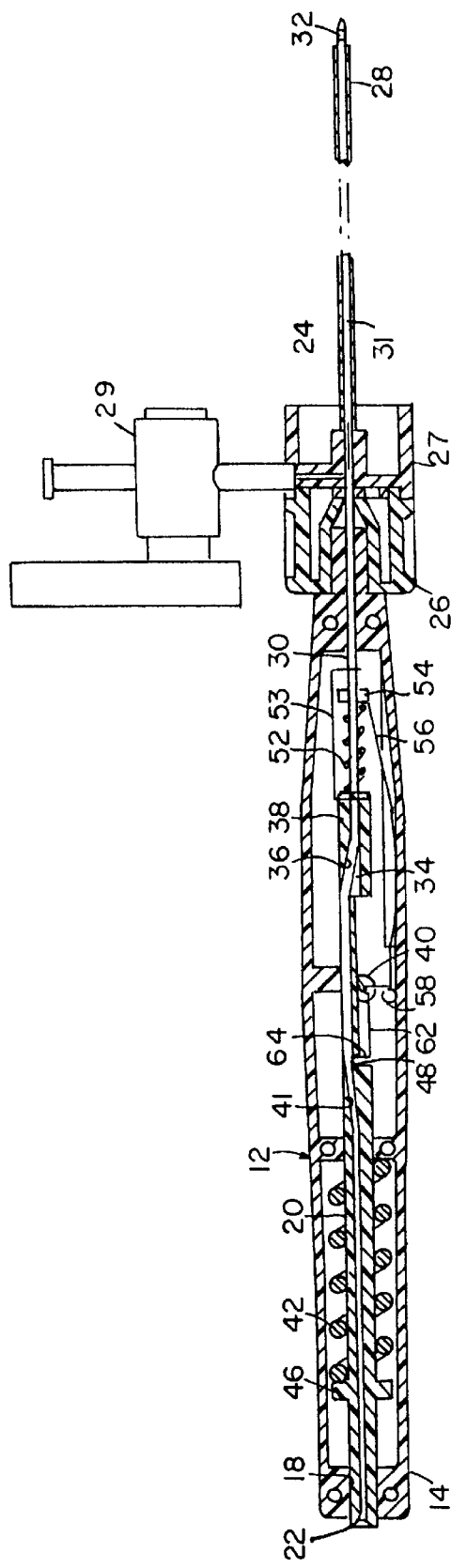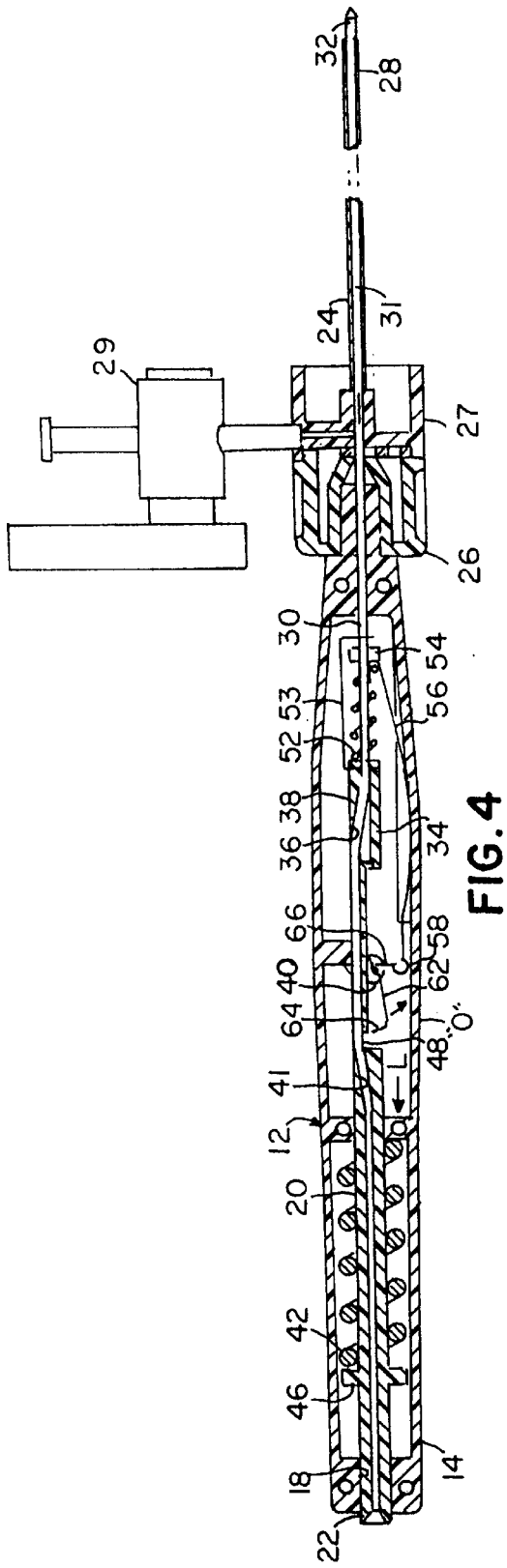

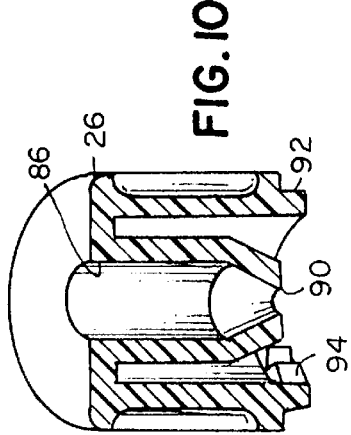
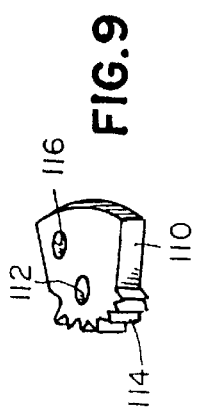
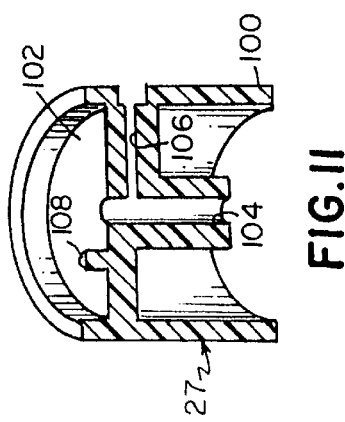
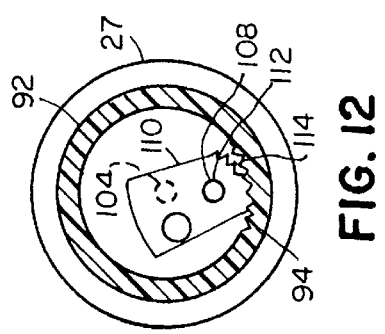
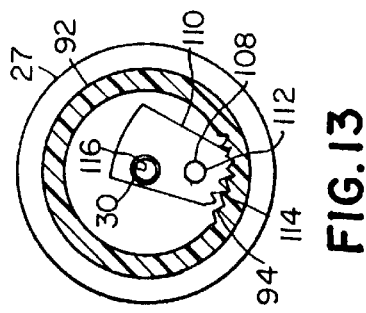

NEEDLE DEVICE

This is a continuation of Ser. No. 361,982, now U.S. Pat. No. 5,514,111, filed 22 Dec. 1994, which is a Division of Ser. No. 57,354, now U.S. Pat. No. 5,376,082, filed 3 May 1993, which is a Continuation-In-Part of Ser. No. 788,253, now U.S. Pat. No. 5,207,647, filed 5 Nov. 1991, all of which are incorporated herein by reference.

BACKGROUND OF THE INVENTION (1) Field of the Invention

This invention relates to needle devices, and more particularly to medical devices for introducing a needle and/or catheter into a body cavity a patient.

(2) Prior Art

The present application incorporates by reference my co-pending application, Ser. No. 07/788,253, filed 11 May 1991.

A veress needle has a hollow, blunt inner needle, spring loaded, within a larger piercing cannula, to permit entry into a body space without laceration of obdominal structures. Several patents which disclose such devices are as follows:

U.S. Pat. No. 5,139,485 to Smith et al, which shows a spring loaded with an acoustic alarm to indicate passage of the needle into a space in a body.

U.S. Pat. No. 5,104,381 to Gresl et al, with a viewable indicator on a stylet to indicate penetration.

U.S. Pat. No. 5,098,388 to Kulkashi et al, having a porthole for receiving a fluid coupling permitting fluid to be passed into the needle.

BRIEF SUMMARY OF THE INVENTION

The present invention provides a needle device which, when cocked, permits penetration of its distal tip into a body until it senses a space or void. The tip, which is a needle, is then retracted automatically and locked within the device, preventing further cutting capabilities of that trocar.

The present invention comprises a needle device having an elongated housing. The housing has a proximal and a distal end. An opening is arranged through the proximalmost end of the housing. A carriage shaft is disposed within the housing and extends slightly outwardly of the proximal opening.

An elongated cannula is attached to the distal end of the housing through a hub. The distalmost end of the cannula has a tip thereon. A needle is slidably disposed through the cannula. The distal end of the needle has a pointed tissue piercing tip. The proximal end of the needle (or trocar) is engaged with a detent assembly arranged at the distal end of the carriage shaft. The needle is hollow, allowing an endoscope (fiber optic camera) or other device to be placed therethrough.

A first compressive spring is arranged within the housing to provide a proximally directed bias onto the carriage shaft. A second compressive spring is arranged within the housing, about the proximal end of the needle, but which spring has less force than the first spring. The distal end of the second spring keeps a forwardly or distally directed bias upon a flange on the needle. The proximal end of the second spring engages the distal end of the carriage shaft. The needle has a proximally extending finger or link which engages a detent assembly. The link rotates the detent assembly to effectuate rearward retraction of the carriage shaft and the needle with respect to the housing.

A valve in the proximal end of the cannula or catheter, is coaxial therewith, and is disposed within a cap and base assembly. Opon removal of the needle from the catheter, the cap and base assembly can be rotated with respect to one another, to open or close the valve therein.

The housing can be removed from the cannula/hub assembly to permit valvable access to the body space through the cannula. A stopcock is attached to the hub assembly to permit insuflation of a patient through the cannula. Insuflation is the pumping of carbon dioxide into a body (peritoneal) cavity to distent the fascis skin.

In operation of the present invention, the needle device is initially cocked by the attending physician, by pressing upon the proximalmost end of the carriage shaft. This causes the detent assembly to become engaged with the carriage shaft and compresses the first spring. The needle is also caused to extend outwardly slightly beyond the distal end of the cannula, causing the exposure of the cutting tip of the needle.

Penetration of skin, tissue and ligaments by gentle force applied to the device into a patient, causes a slight rearward pressure and movement on the needle, simultaneously compressing the second spring and causing the link to move to a position that upon any forward motion of the needle link assembly, the link will rotate the detent assembly and thus release the carriage.

Upon entry of the needle into the body space, the needle is advanced distally very slightly by bias of the second spring thereagainst. This slight forward or distal advance of the needle causes the link attached to it to trip the detent assembly, thus releasing the carriage shaft from capture, whereupon the first, more powerful spring pushes the carriage shaft and attendently attached needle rearwardly or proximally, with an audible sound. This causes the needle to also be retracted proximally within the cannula. The proximal end of carriage shaft is also caused to extend out through the opening in the proximal end of the housing, to provide a visual indication of penetration into the body space, as well as the audible indication of such entry. A bore extends longitudinally through the carriage shaft, and is in communication with the bore in the needle. An optical device such as an endoscope, or a medicament supply may be disposed within such bore to permit visualization of the puncture and body organ and/or supply of medicaments therein.

Dissassembly of the cannula from the housing and opening of the bore of the catheter permits delivery of medicaments or other medical devices. The valve could be closed to close the bore through that cannula. A valved side port through the base permits the valve at the proximal end of the cannula to be closed (or open) while permitting supply of medicaments therethrough simultaneously with optics or other medicaments being disposed through the valve in the base.

It is apparent that this device may also be used to locate/enter other spaces or potential spaces in the body where there is less resistance than in the surrounding tissue, such as with the pneumothorax needles, drainage of absesses or the like.

BRIEF DESCRIPTION OF THE DRAWINGS

The objects and advantages of the present invention will become more apparent when viewed in conjunction with the following drawings, in which:

FIG. 1 is a side elevational view insection of an veress needle device in a "packaged" configuration;

FIG. 2 is a view similar to FIG. 1, showing the veress needle device in its "cocked" configuration;

FIG. 3 is a view similar to FIG. 1, showing the veress needle device during penetration of tissue;

FIG. 4 is a view similar to FIG. 1, showing the veress needle device just as it enters an open space;

FIG. 9 is a perspective view of the valve member which rotatively mates with the base;

FIG. 10 is an enlarged longitudinal sectional view of the catheter cap;

FIG. 11 is an enlarged longitudinal sectional view of the catheter base;

FIG. 12 is a view taken along the lines XII—XII of FIG. 8, with the needle removed and the valve closed; and FIG. 13 is a view taken along the lines XIII—XIII of FIG. 7, and the valve opened.

DESCRIPTION OF THE PREFERRED EMBODIMENT

Figure 5:
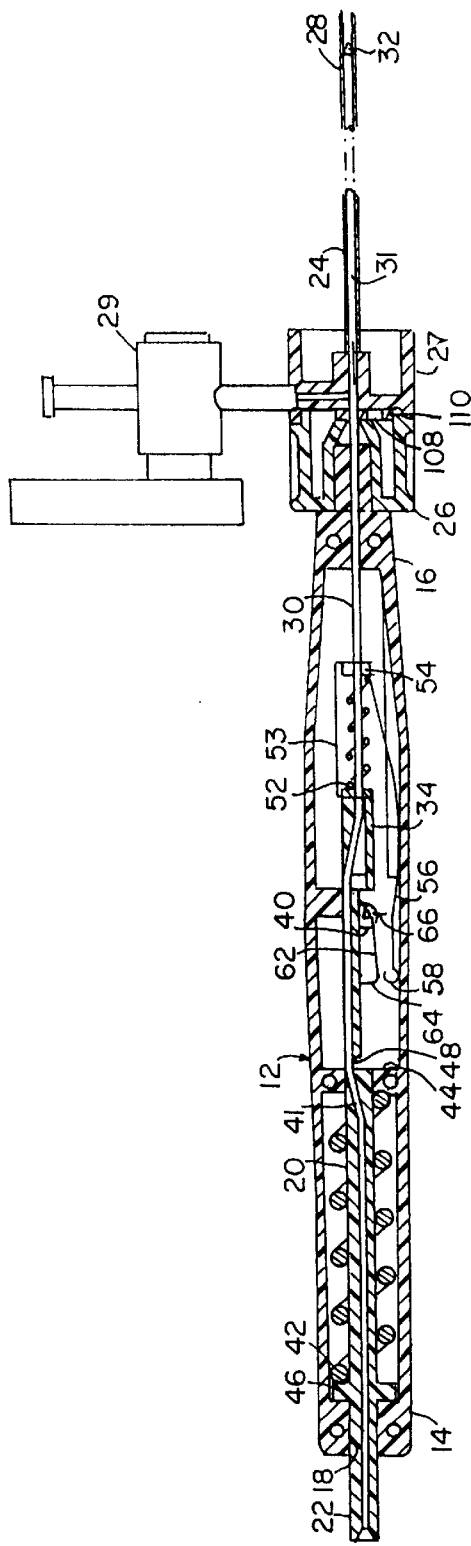
FIG. 5 is a view similar to FIG. 1, showing the veress needle device after it has entered the epidural space.

Referring now to the drawings in detail, and particularly to FIG. 1, there is shown a veress needle device 10, having an elongated housing 12 having a proximal end 14 and a distal end 16. A proximal opening 18 is arranged through the proximal end 14 of the housing 12. A longitudinally slidable carriage shaft 20 is disposed within the housing 12, and has a proximal end 22 which extends slightly outwardly of the proximal opening 18, when the veress needle device is shown in its "packaged" or "shipping" configuration depicted in FIG. 1.

An elongated cannula (or catheter) 24 is attached to the distal end 16 of the housing 12 through a mating cap 26, shown in an enlarged sectional view in FIG. 10. The cannula 24 has a tip 28 on its distalmost end. A tubular needle 30 extending from the distal end 16 the housing 12 is slidably disposed within the lumen of the cannula 24. The needle 30 has a pointed tissue piercing tip 32 on its distalmost end. A discharge opening 33 is disposed proximally adjacent the tip 32, the opening 33 being in fluid communication with a lumen 31 in the tubular needle 30. A base 27 is arranged on the proximal end of the cannula 24. The base 27 has a central bore 104 which extends longitudinally therethrough and is in communication with the lumen 31 in the needle 30. A side valve 29 is attached to the side of the base 27 and is in fluid communication through a channel 106 with the bore 104, as shown in FIG. 11.

Figure 6:
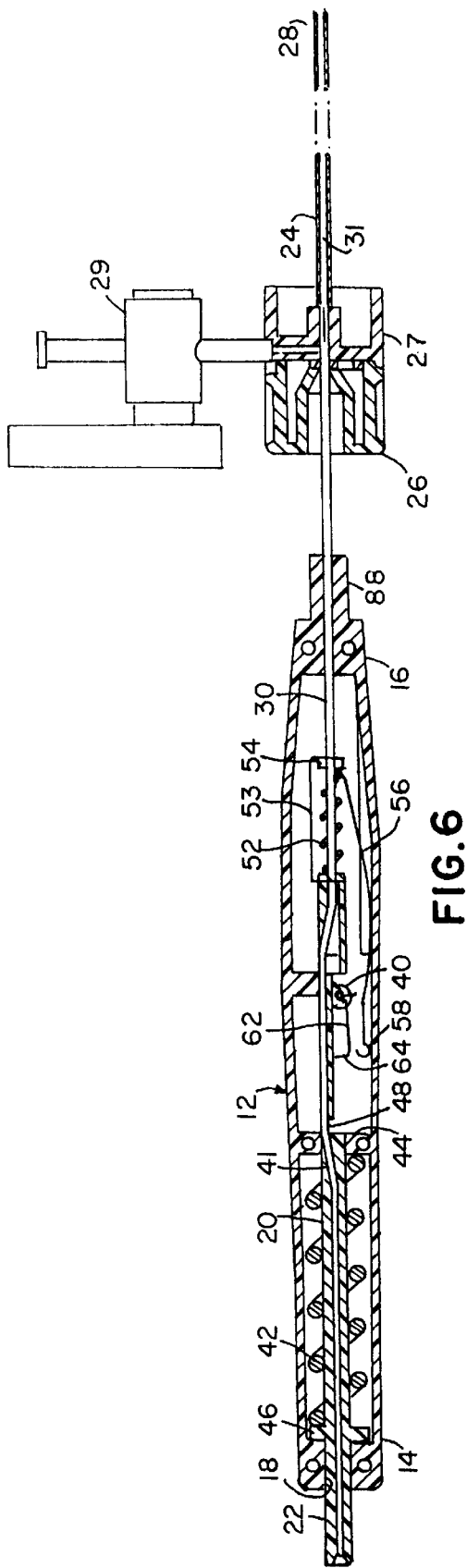
FIG. 6 is a view of the needle device being removed from its catheter tip.
Figure 6A:
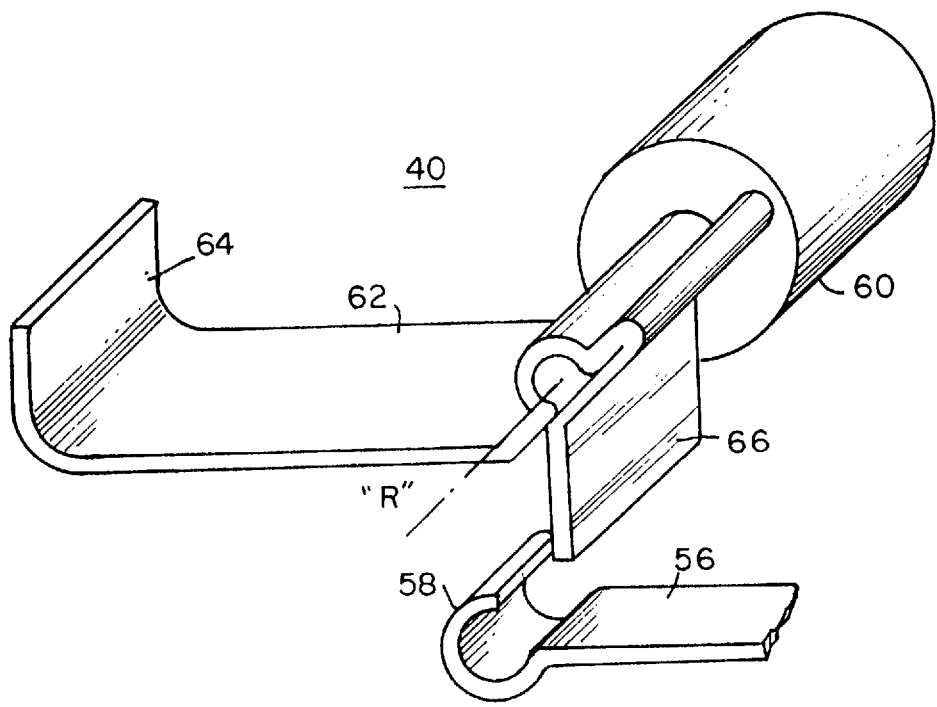
FIG. 6A is a perspective view of a detent assembly arranged within the housing of the veress needle.

The needle 30 has a proximal end 34 which extends into the distal end 16 of the housing 12 and which slidably engages a tapered channel 36 in a flange 38 on the distal end of the carriage shaft 20, which is adapted to facilitate engagement and disengagement of a detent assembly 40, shown more clearly in FIG. 6A.

A first compressive spring 42 is arranged within the housing 12 between an abutment 44 therein disposed about the carriage shaft 20 and an annular flange 46 secured to the carriage shaft 20 near its proximal end 22. The first compressive spring 42 provides a rearward or proximally directed bias onto the carriage shaft 20. A longitudinal bore 41 extends through the carriage 20, and is in fluid communication with the bore 31 of the needle 30.

A notch 48 is arranged transversely about the mid-point of the carriage shaft 20, as shown in FIG. 1.

A second compressive spring 52 is disposed about a portion of the proximal end 34 of the needle 30. The second spring 52 has a distal end which abuts an annular flange 54 which is disposed about the approximate mid-point of the needle assembly 30. The second spring 52 has a proximal end which is in abutting engagement with the distalmost end of the carriage shaft 20 and the flange 38 thereon. An elongated resilient finger or link 56 is attached to the flange 54 and extends rearwardly therefrom. The link 56 has a "J" shaped distalmost tip 58 which engages the detent assembly 40. A "U" shaped clip 53 has an end which engages the flange 38 and another end which acts as an abutment to the flange 54, this other end slidably receiving the needle therethrough.

Figure 7:
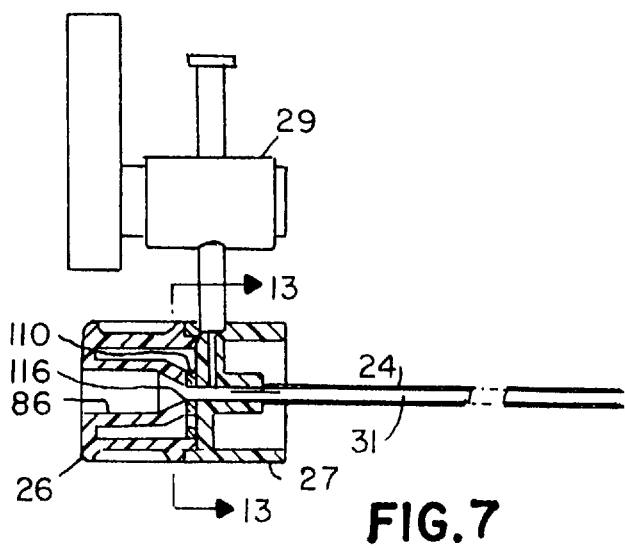
FIG. 7 is an enlarged longitudinal sectional view of the hub, base and cannule in a valve open orientation.
Figure 8:
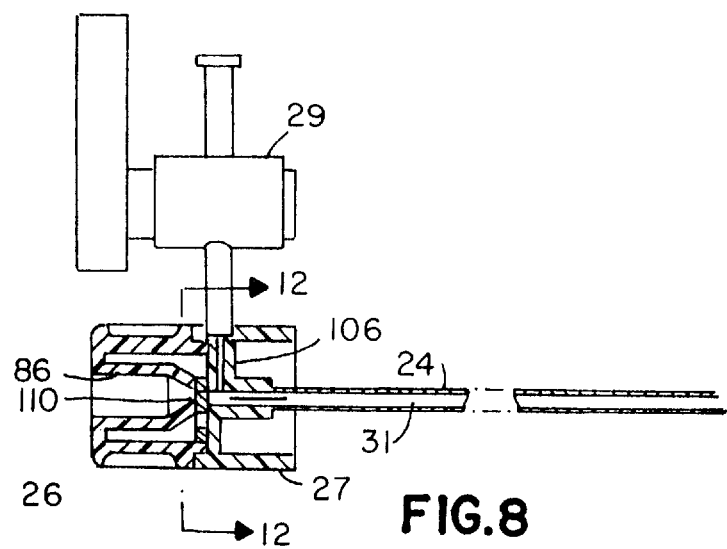
FIG. 8 is an enlarged longitudinal sectional view of the hub, base and cannula in a valve closed orientation.

The detent assembly 40, shown more explicitly in FIG. 6A, comprises a pivot hub 60 which is pivotably secured to an inside wall of the housing 12. The pivot hub 60 is of generally cylindrical configuration and has an axial post, not shown, on which a spring leg 62 is fixed. The leg 62 has a distal toe 64 arranged at a right angle thereto. The toe 64 is arranged to engage the notch 48 on the carriage shaft 20. A release flange 66 extends from the proximal end of the leg 62, as shown in FIG. 7. The tip 58 of the link 56 is juxtaposed to engaged and pull on the release flange 66 so that the toe 64 is pivoted from the notch 48, thus releasing the carriage shaft 20, in a manner described hereinbelow. 50 adjacent the shoulder 48 of the carriage shaft 20.

The distalmost tip 58 of the link 56 is arranged to mate with the toe 64 and give it a slight "pull" to cause it to rotate (counter clockwise as shown in the drawings) so as to lift the toe flange 64 from the notch 48 in the carriage shaft 20.

The cannula 24 has the mating cap 26 on its proximal most end, as shown in FIGS. 1–6. The cap 26, has a tapered central bore 86, which sliddably mates with a tapered projection 88 on the distal end 16 of the housing 12. The cap 26 has an opening 90 at the distal end of the bore 86. An annular wall 92 defines the side perpheral surface of the cap 26. An angular array of gear teeth 94 are disposed on the inner perpheral surface of the distal end of the annular wall 92, as shown in FIG. 10.

A base 27, shown in FIGS. 1–6, but shown more clearly in section, in FIG. 11, comprises an annular wall 100 having a disc 102 molded adjacent its proximal end. The disc 102 has a central bore 104 arranged therethrough. A channel 106 is arranged through the wall 100 and is in communication with the bore 104. A pivot axis 108 extends proximally off of the disc 102 between the wall 100 and the bore 104.

An elongated valve member 110, shown in cross-section in FIGS. 1–6, is shown in perspective in FIG. 9, has an opening 112 across one end thereof, which mates on the pivot axis 108 off of the disc 102 on the base 96. The valve member 110 has an arrangement of gear teeth 114 on one end adjacent its opening 112. The valve member 110 has an arrangement of gear teeth 114 on one end adjacent its opening 112. The valve member 110 has a circular second opening 116 on the other end thereof, the second opening being of a diameter similar to the opening 90 in the cap 26 and the central bore 104 in the base 27. The needle 30 is sized to slide through each of these openings when they are in longitudinal alignment, as is the case shown in FIG. 10.

In assembly of the cannula 24, the valve member 110 is mounted with its first end opening 112 on the pivot axis 108.

The cap 26 then fits against the disc 102 with the distal lip of its walls 92 mating within the proximal lip of the walls 100 of the base 27, with the bore 90 in alignment with the second end opening 116 of the valve member 110 and the bore 104 of the base 27. The teeth 114 of the valve member 110 are engaged with the teeth 92 on the inner distalmost lip of the wall 92 of the cap 26. Once the needle 30 has been removed from the catheter 30, the valve member 110 may be arcuately pivoted about pivot axis 108 on the cap 27 by rotation of the cap 26 therewith, because of the interengagement of the gear teeth 114 and 94 therebetween. Such a movement of the valve member 110 is shown in FIGS. 12 and 13, where FIG. 12 indicates the position of the valve member 112, now closed, once the needle 30 has been withdrawn from the aligned openings 90, 116 and 104.

The side valve 29, shown in FIGS. 1–6, mates with the channel 106 in the base 96 to permit fluid communication with the bore 104 and the canulea 24, once the needle 30 has been withdrawn therefrom, permitting access to the body cavity therewith.

In operation of the needle device 10 the attending physician "cocks" it from its "packed" state shown in FIG. 2 to its "cocked" state by pressing the proximal end 22 of the carriage shaft 20 distally, or to the right, as shown in FIG. 2, thereby compressing the first spring 42 and bringing the notch 50 into mating engagement with the flange 72 of the outwardly biased U-shaped spring 64. The tip 32 of the needle 30 is also at this time, once the device 10 has been cocked, to be caused to extend about 2 mm. beyond the distalmost end of the cannula tip 28, and simultaneously permitting the cutting portion of the needle assembly 30 to be distally exposed.

Gentle but constant pushing force by the physician on the needle device 10 penetrates the patient's skin, soft tissue and ligaments, and causes the needle assembly 30 including the link 56, to be pushed-back into the catheter 24 slightly, (to the left) as shown in FIG. 3, and also compressing the second compressive spring 52 slightly, and moving the tip 58 of the link 56 proximally past the pivot hub 60.

Upon entering a body cavity the needle 30 encounters less resistance, and is therefore caused to advance slightly, for this example about 0.25 mm. because of its forward (distally directed) bias from the second compressive spring 52 acting upon the annular flange 54 secured thereto, the needle 30 being shown thusly in FIG. 4. The distal tip 58 of the link 56 mates with the toe 64 extending off of the hub 60.

As the needle 30 advances for example, about 0.25 mm. Upon meeting with sudden diminished resistance upon entering the epidural space it also causes the link 56 to advance forwardly a corresponding amount. The frontwardly moving (distal) end 58 of the link 56 having been engaged with the release flange 66 of the pivot hub 60, causes the pivot hub 60 to rotate slightly, about its axis of rotation "R", counter-clockwise as shown in the drawings, to cause the rotation of the leg 62 as well, lifting the toe flange 64 out from locking engagement in the notch 48 of the carriage shaft 20, as indicated by the arrow "O" in FIG. 4.

The first compressive spring 42, being stronger than the second compressive spring 52 is thus released, so as to push the carriage shaft 20 rearwardly, or the left, as shown in FIG. 4, by an arrow "L", this occurring with an audible click, as the flange 46 hits the proximal wall of the housing 12, the spring 42, as shown in FIG. 5, by the pushing of the proximal end 22 of the carriage shaft 20 out of the proximal opening 18 in the housing 12. During the rearward travel of the carriage shaft 20, the needle assembly 30 to which the carriage shaft 20 is engaged, is also pulled proximally (rearwardly) by the first compressive spring 42, as depicted in FIG. 5.

Upon encountering of the void or epidural space, the needle 30 no longer feels the resistance to its advance and retracts as aforementioned.

FIG. 6 shows the housing 12 and its enclosed/attached needle 30 being removed from the cannula 24, to facilitate delivery of medicaments (or other catheters or medical devices) through the cannula 24 after the distal end of the needle 30 has been removed therefrom. Additionally, the cannula 24 itself, 28 could also be directed further into the body duct.

The valve member 110, as aforementioned, can then be closed to await need for re-opening of the cannula 24 for introduction of a medical device such as an endoscope, or fluid therethrough. The valve 110 could be replaced by a duckbill valve or a soft, penetrable material with a slit therethrough, not shown. The side valve 120 in the hub assembly also permits supplemental fluid introduction capabilities through the cannula 24 also.

Thus, what has been shown and described is a unique needle device suitable particularly for veress-type procedures, which permits single handed advance into body tissue, and when the needle (trocar) upon entering an body space and sensing no resistance to further forward advance, minutely advances on its own, well within distance limitations of small body space, only to trigger its own immediate retraction, removing the cutting and piercing component from exposure, presenting to that space a cannula tip for subsequent adaptation to a medical device on medicament supply source upon removal of the needle (trocar) and drive assembly form the cannula shaft.

I claim:

1. A method of delivering medical treatments to a body comprising the steps of:

advancing into a body space a medical delivery device having an elongated housing with a piercing needle attached at a distal end thereof, said piercing needle being arranged within a hollow catheter member also attached to said housing, said hollow catheter member and said piercing needle having a spring arrangement within said housing connected so as to effect relative movement between said catheter member and said piercing needle during use of said delivery device;

puncturing a body space by said piercing needle which needle extends distally beyond the distal end of said catheter member;

moving said catheter member relative to said piercing needle by action of said spring arrangement in said housing, upon said medical delivery device losing resistance to forward motion in a body being pierced; and providing an audible indication of loss of resistance to forward motion in a body being pierced, by said delivery device, to the operator of said delivery device.

2. The method of claim 1, including the step of:

providing a visual indication of loss of resistance to forward motion of said delivery device to the operator of said delivery device.

* * * * *